US006426215B1

(12) United States Patent
Sandell

(10) Patent No.: US 6,426,215 B1
(45) Date of Patent: Jul. 30, 2002

(54) PCR PLATE COVER AND MAINTAINING DEVICE

(75) Inventor: Donald R. Sandell, San Jose, CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/826,854

(22) Filed: Apr. 6, 2001

(51) Int. Cl.[7] .................................................. C12M 1/22

(52) U.S. Cl. .................................. 435/305.3; 435/305.4

(58) Field of Search ........................ 422/102; 435/287.2, 435/288.4, 305.3, 305.4

(56) References Cited

U.S. PATENT DOCUMENTS 5,282,543 A 2/1994 Picozza et al. ............. 220/255
5,582,665 A 12/1996 Eigen et al. .................. 156/69
5,604,130 A * 2/1997 Warner et al. .............. 220/523
5,721,136 A * 2/1998 Finney et al. ............ 220/359.3
5,741,463 A * 4/1998 Sanadi ........................ 422/101
6,159,368 A 12/2000 Moring et al. ......... 210/321.75
6,251,622 B1 * 6/2001 Serhan et al. ................. 435/18

* cited by examiner

*Primary Examiner*—David A. Redding
(74) *Attorney, Agent, or Firm*—Finnegan, Henderson, Farabow, Garrett & Dunner LLP

(57) ABSTRACT

A cover for a PCR plate having multiple wells including a rigid sheet, and a resiliently compliable sheet cooperating with one side of the substantially rigid sheet to a press a sealing sheet against the surface of the PCR plate to maintain a seal in the wells. The cover further includes at least one retaining device attached to the rigid sheet to engage with the PCR plate and retain the substantially rigid sheet and the resiliently compliable sheet in a condition to press the sealing sheet against the surface of the PCR plate. Also disclosed is an assembly that includes a PCR plate and a cover that is designed to prevent sample loss.

37 Claims, 7 Drawing Sheets

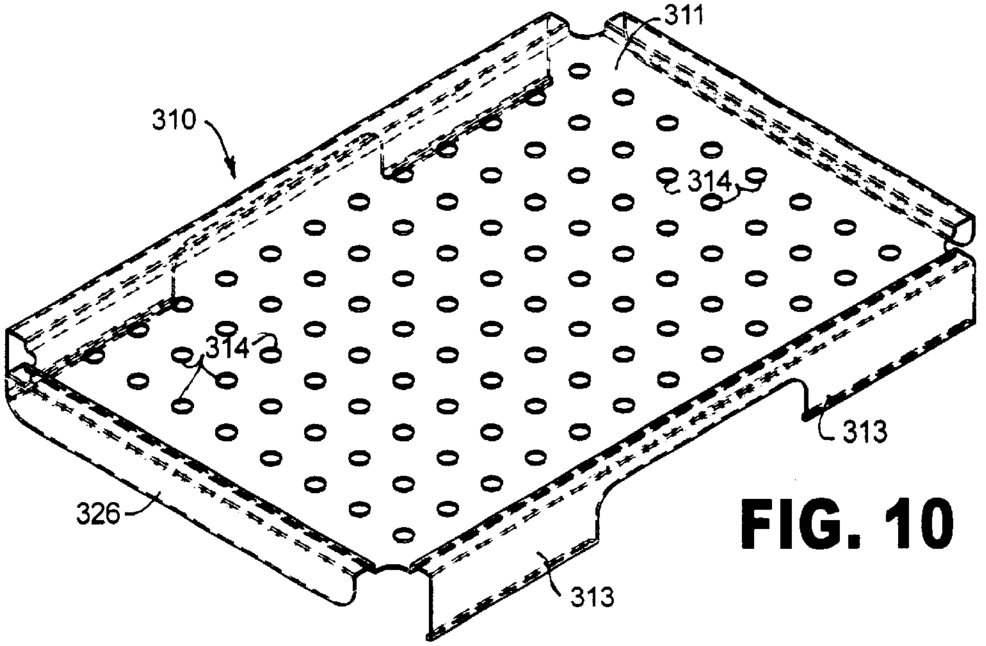
FIG. 10
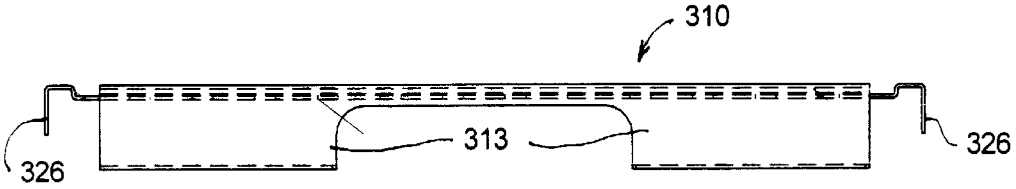
FIG. 11
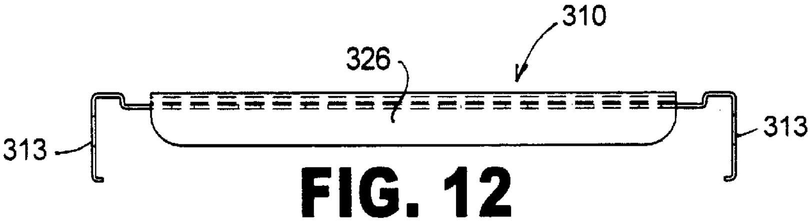
FIG. 12
FIG. 14
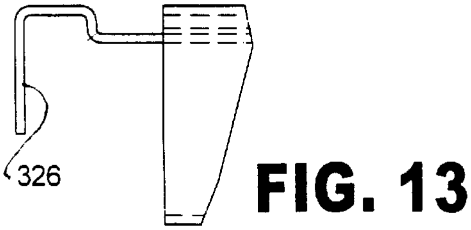
FIG. 13
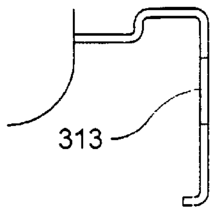

PCR PLATE COVER AND MAINTAINING DEVICE

BACKGROUND OF THE INVENTION

1. Field of the Invention

The present invention relates to PCR apparatus. More particularly, the present invention relates to vessels, containers, kits, assemblies, and methods for effectively conducting PCR on samples.

2. Description of the Related Art

Biological testing has become an important tool in detecting and monitoring diseases. In the biological testing field, thermal cycling is often used to amplify nucleic acids by performing polymerase chain reactions (PCR), for example, and other reactions. PCR typically is carried out in containers such as tubes, plates, or trays having multiple wells. In such containers, reagents such as DNA polymerase, nucleotides, oligonucleotide primers, buffers, and a DNA template are exposed to thermal cycling to promote amplification of the DNA template. See also U.S. Pat. Nos. 6,015,534; 5,710,381.

The wells in PCR plates typically are sealed during the PCR cycling to minimize volume loss and contamination of material contained within. Heat-sealed blankets, adhesive blankets, caps, or other such means are often used to seal the wells in the PCR plates. For example, U.S. Pat. Nos. 5,721,136 and 6,127,188 propose materials that control the level of sample loss during chemical reactions. Additional filter material may be used to process samples within the PCR plate wells. For example, commonly assigned U.S. Pat. No. 6,159,368, the entire disclosure of which is incorporated by reference herein, describes, among other things, a multi-well micro-filtration apparatus that provides for the separate processing of filtrate from at least one well of a multi-well micro-filtration device.

Because of the relatively thin layer of adhesive on an adhesive blanket, for example, and the pressure generated within the wells, a compliant pad typically is placed between the blanket and a cover to assure a robust seal between the blanket and the individual wells within the tray. These compliant pads are typically pads that are flexible and assume the shape of the material they are pressed against. The compliant pad may be a silicone or foam pad cut to fit on top of the PCR plate.

Thermal cyclers, such as those described in U.S. Pat. Nos. 5,475,610 and 5,602,756, both incorporated by reference herein in their entirety, are typically used to amplify nucleic acid templates by PCR. With the introduction of direct-reading optical PCR systems, such as the 5700, 7700, and 7900HT systems from Applied Biosystems of Foster City, Calif., holes were added to the compliant pads allowing real time visual access by the optical system to the samples in the wells through the optically clear blanket. See also U.S. Pat. No. 5,928,907 and 6,015,674, both incorporated by reference herein in their entireties.

Real time visual monitoring of samples typically is practical with 96 well plates. Generally, with higher density plates having increased numbers of wells, the typically higher tolerance build-up between the plate and dimensionally unstable compliant pads may present a need for addressing the increased tolerance.

Furthermore, typical compliant pads may not always be acceptable for manual or robotic handling. Compliant pads could be inadvertently picked up by a robotic mechanism by the upper tray in the stacker and get lodged between the PCR plate and the thermal cycling block. Further, a die-cut compliant pad could move, causing partial or complete blockage of the optical path.

Additionally, heat sealed sheet-covered PCR plates typically could become warped because of the shrinkage of the heat sealed covers and plates, making them difficult or impossible to pick up with standard robotic mechanisms, particularly if used with heat-sealed covers or after thermal cycling.

Die-cut adhesive compliant covers also could be difficult to align and were not suitable for reuse. These covers could allow a robot grip inadvertently to pick up two trays at the same time by clinging to the bottom surface of the upper tray in a stacker.

There exists a need for a high tolerance rigid cover that is easily installed, economical, and maintains the fit of the PCR plate to enhance proper robotic handling, such as stacking and handling, and preserving the sample contained within. Additionally, the rigid cover should be able to withstand the conditions associated with thermal cycling, such as the heat, without unacceptable deforming, warping, or buckling. The rigid cover should also not act as a heat sink, thereby decreasing the efficiency of the thermal cycling process. Finally, the rigid cover should be chemically compatible with any samples and reagents used in the process and should not affect their chemical reactions.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention is directed to a cover for retaining a sealing sheet on a surface of a PCR plate having sample wells depending from and opening through the surface, and a peripheral wall surrounding the sample wells and connected to a base. The cover includes a substantially rigid sheet capable of maintaining the surface of the PCR plate in a pre-thermal-cycling shape during a PCR thermal cycling process, and a resiliently compliable sheet cooperable with one side of the substantially rigid sheet to press the sealing sheet against the surface of the PCR plate to maintain a seal in the wells. At least one retaining device is attached to the substantially rigid sheet to be engagable with the PCR plate to retain the substantially rigid sheet and the resiliently compliable sheet in a condition to press the sealing sheet a against the surface of the PCR plate. The retaining device may be embodied in various forms and multiple retaining devices may be used In another aspect, the advantages and purpose of the invention are realized and attained by an assembly for processing samples in PCR, including a PCR plate having sample wells depending from and opening through a surface in the plate, and a peripheral wall surrounding the sample wells and connected to a base, and a cover for the PCR plate. The cover includes a substantially rigid sheet capable of maintaining the surface of the PCR plate in a pre-thermal-cycling shape during a PCR thermal cycling process and a resiliently compliable sheet cooperating with one side of the substantially rigid sheet and capable of pressing a sealing sheet against the surface of the PCR plate to maintain a seal in the wells. At least one retaining device is attached to the substantially rigid sheet and engagable with the PCR plate to retain the substantially rigid sheet and the resiliently compliable sheet in a condition to press the sealing sheet against the surface of the PCR plate.

Additional features and advantages of the invention will be set forth in the description which follows, and in part will be apparent from the description, or may be learned by practice of the invention. The objectives and other advantages of the invention will be realized and attained by the apparatus, assemblies, kits, and methods particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate exemplary embodiments of the invention and, together with the description, serve to explain the objects, advantages, and principles of the invention. In the drawings.

FIG. 10 is a perspective view of a further embodiment of the invention;

FIG. 11 is a side elevation of the embodiment shown in FIG. 10;

FIG. 12 is an end elevation of the embodiment shown in FIG. 10;

FIG. 13 is an enlarged fragmentary end elevation of the embodiment shown in FIG. 10; and FIG. 14 is an enlarged fragmentary side elevation of the embodiment shown in FIG. 10.

DETAILED DESCRIPTION OF EXEMPLARY EMBODIMENTS

The present invention relates to processing, packaging, storing, and handling biological samples, particularly in PCR systems. More particularly, the present invention relates to a cover that cooperates with experimental carriers including plates or trays, such as for PCR testing, such that the carriers have desirable handling, stacking, and containing properties. Furthermore, the containers also may promote analysis of any material stored within.

Reference will now be made in detail to the present exemplary embodiments of the invention, examples of which are illustrated in the accompanying drawings.

Either of PCR plates 30 or 40, such as those depicted in FIG. 1*a* or FIG. 1*b*, respectively, may be used with the cover of the present invention, described in more detail below. The PCR plates are typically is formed of molded plastic material that is compatible with (does not react with) a PCR reagent and are of a rectangular shape and size of the industry standard for microtiter well plates, i.e., 5.03"×3.37" (128 mm×85 mm). Each plate 30, 40 has an array of wells 31, 41 that may vary in number for the same plate size, e.g., 24, 96, 384, 1536 wells ranging in size from 5–20 $\mu$l for the plate 30 and 25–200 $\mu$l for the plate 40. In use, the wells 31, 41 are typically filled to if one half the well volume or less.

Figure 1A:
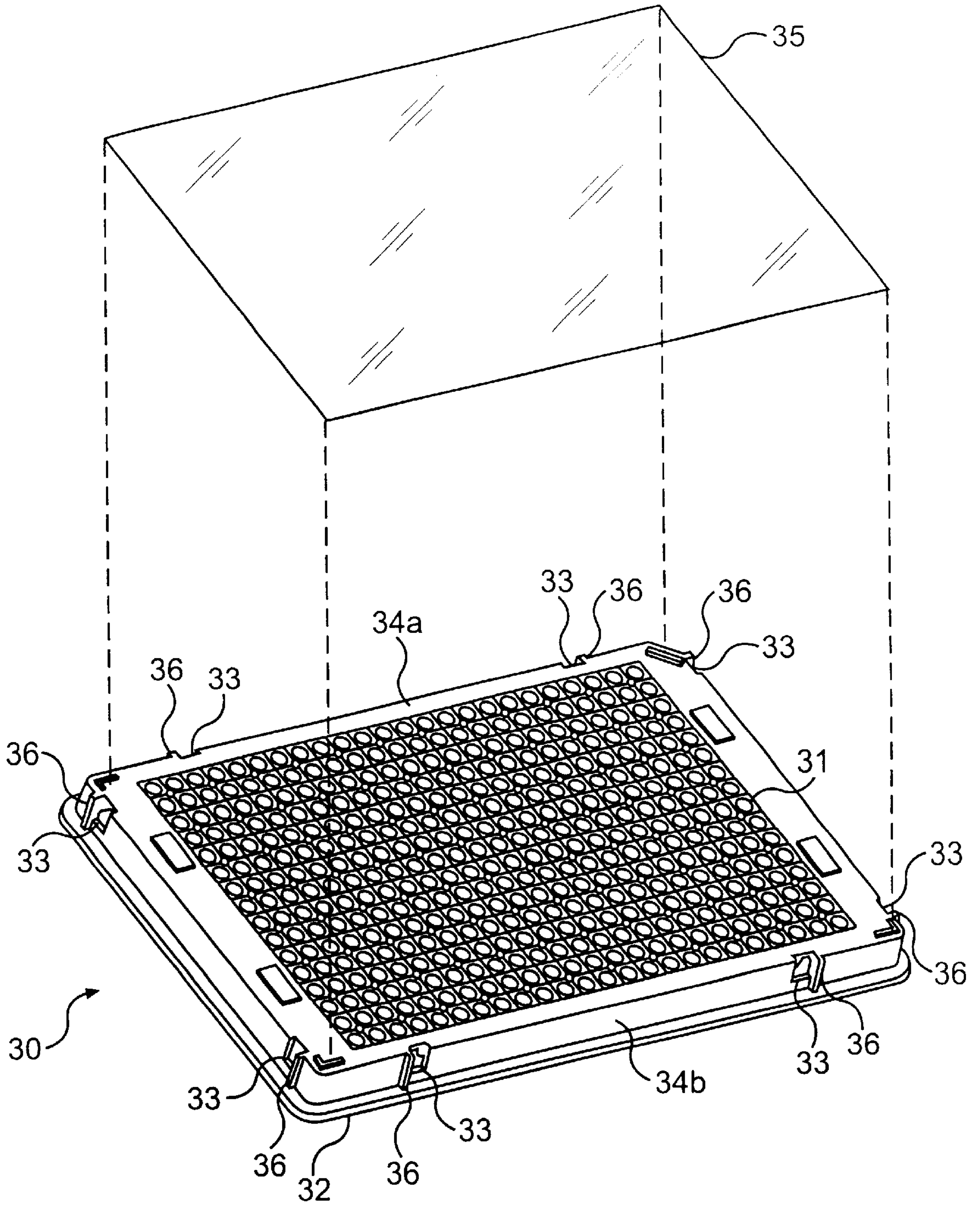
FIG. 1*a* is a perspective view illustrating a 384-well PCR plate that may be used with an apparatus of this invention.

As shown in FIG. 1*a*, the wells 31 depend from and open through a top surface 34*a* of the plate 30. The top surface 34*a* may be planar, curvilinear, or other shape. The exemplary embodiment shown in FIG. 1 depicts a plate 30 having 384 wells, but any number of wells in any type of configuration is possible. After at least some of the wells 31 are partially filled with the reagents, a layer of material 35, typically a thin plastic film, may be placed on the top surface 34*a* so as to cover and seal the wells 31 to prevent material within the wells 31 from evaporating or becoming contaminated. The material layer 35 may provide a seal for the wells 31, and may be placed thereupon by adhesive, heat shrink, surface tension, or other similar layering process. A peripheral wall 34*b*, that has four sides in a rectangular PCR plate, depends from the surface 34*a* to a base 32, about the length of a typical well 31. The base 32 may be wider than the rest of the apparatus and allows the plate 30 to rest more securely against a surface. Furthermore, the base 32 allows the bottom of the PCR plate 30 to be more easily detected so as to prevent accidental upside-down placement of the plate 30. Also, the base 32 allows for ease of transport of the PCR plate 30 and cover 10 or 20, depicted in FIGS. 2–9. Finally, a plurality of receiving apertures 33 serve to accommodate projections from a robotic system (not shown) used to index, register, align, and transport the plates 30 during PCR operation. In proximity to the receiving apertures 33 are a system of ribs 36, which may be used for alignment, as will be described in more detail below. Furthermore, it should be noted that the PCR plate 30 is shown merely as an example of a suitable PCR plate that can be used with this invention, and is not intended to limit the type of PCR plates that can be used with this invention, and the exemplary embodiments described below.

Figure 1B:
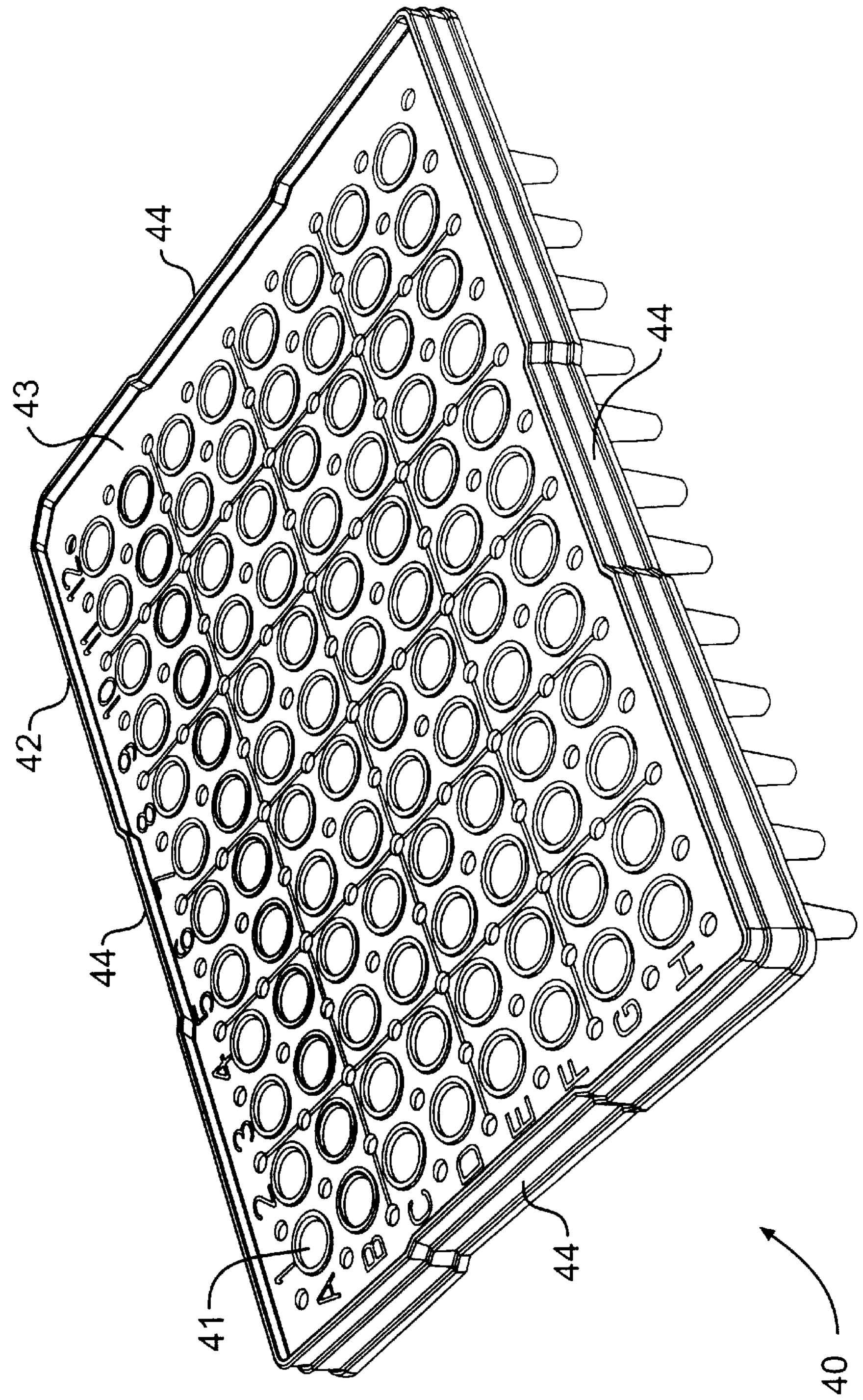
FIG. 1*b* is a perspective view showing a 96-well PCR plate that may be used an apparatus of this invention.
Figure 2:
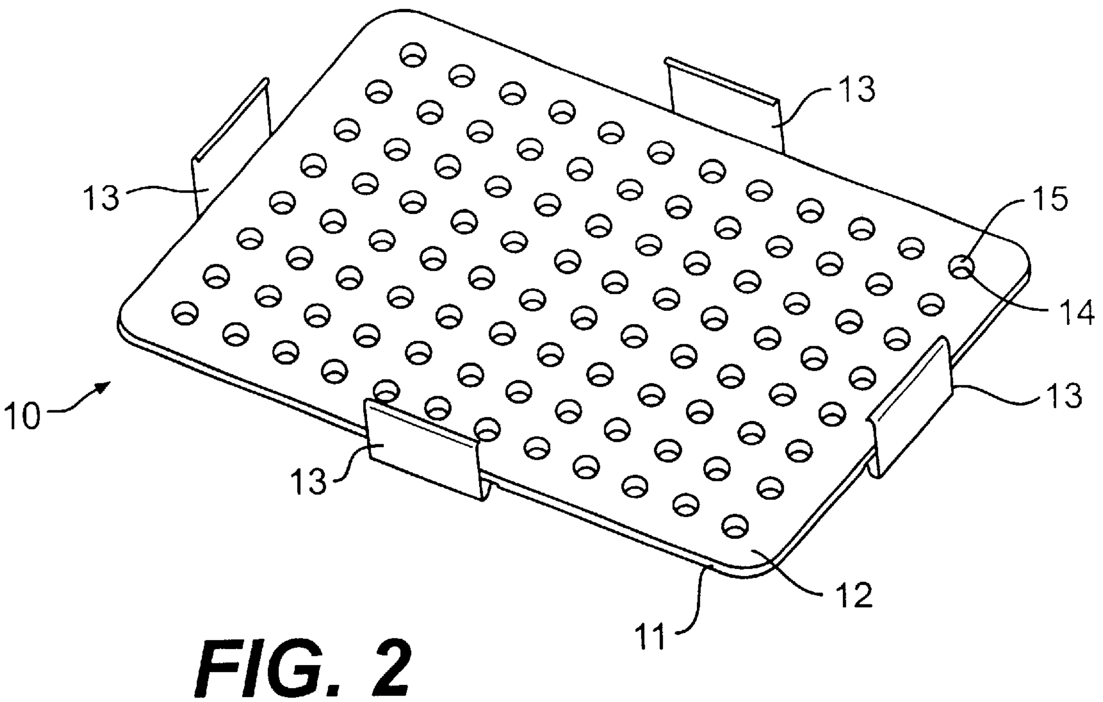
FIG. 2 is a perspective view showing an apparatus according to an exemplary embodiment of the present invention for a 96-well plate.
Figure 3:
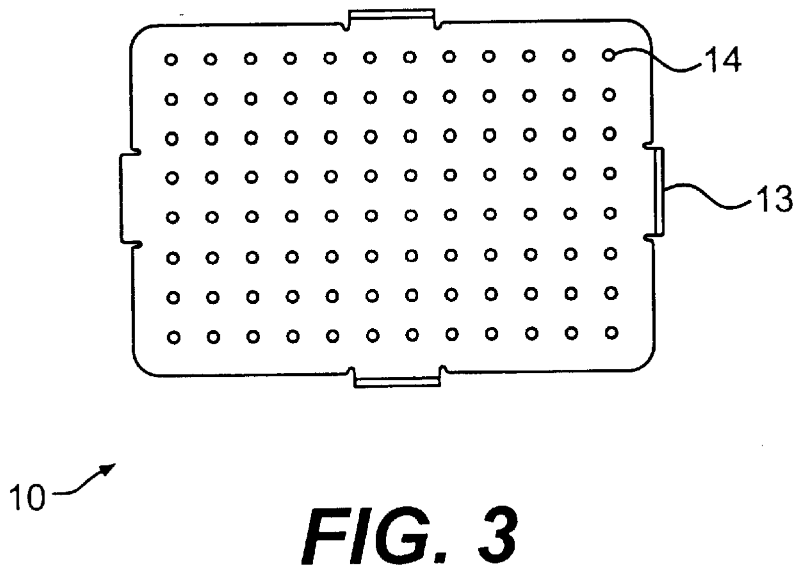
FIG. 3 is a bottom plan view of the apparatus shown in FIG. 2.
Figure 4:
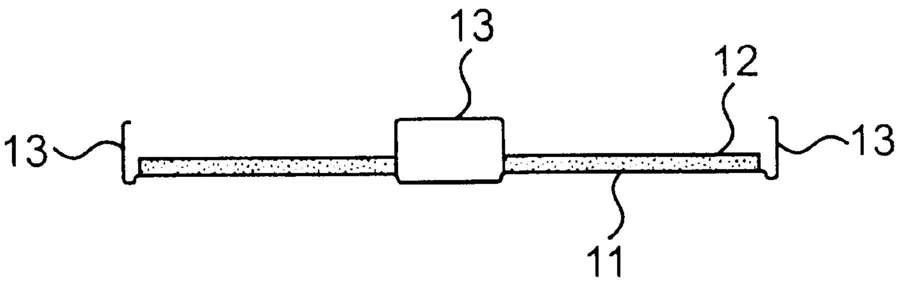
FIG. 4 is a side view of the apparatus shown in FIG. 3.

For example, the PCR plate 40 shown in FIG. 1*b* may be used with the apparatus of this invention. Plate 40 has 96 wells 41 in the figure, but other numbers of wells are possible. A top surface 43 contains the openings to the wells 41. This top surface 43 may be planar, although other shapes, such as curvilinear, also may be possible. A peripheral wall 42 surrounds the top surface around its periphery and has retaining device cooperating notches or indentations 44.

An exemplary embodiment of the PCR tray cover of the present invention is shown in FIGS. 2–5 and is designated generally by reference numeral 10. As embodied herein and referring to FIG. 1, the cover 10 having a substantially planar and rigid exterior shell 11 and a resiliently compliable interior material 12. The exterior shell 11 preferably is a thin, relatively rigid material, such as a sheet of metal, such as aluminum. For example, a 0.02" thickness aluminum sheet may be used. However, the thickness of the exterior shell 11 depends on the nature of the material used. The exterior shell 11 may also be made of other metals, plastics, ceramics, glass, or other it suitable material. The rigidity of the exterior shell 11 preferably should be enough to maintain the pre-thermal-cycling shape of the PCR plate even after a typical PCR thermal cycling, approximately 60° to 100° C. Thus, heat, as encountered by a PCR thermal cycling, should not be able to affect the rigidity and pre-thermal-cycling-exposed shape of the exterior shell 11. Further, the exterior shell 11 may be opaque or translucent, depending on the type of material used. Color-coding the exterior shell 11 may also help to distinguish different sizes and styles to facilitate ease of use with particularly shaped or sized PCR plates or trays.

One or more retaining devices 13 project from the exterior shell 11. Retaining devices 13 may releasibly engage, hold, grasp, clamp, or clip the apparatus 10 to the PCR plate 30. Apparatus 10 may be disengaged from plate 30 manually or by a robot. The retaining devices 13 are continuous with the one or more sides of the exterior shell 11. Thus, for ease of manufacturing, the retaining devices 13 are made from the same material as that of the exterior shell 11, such that the shell 11 having one or more retaining devices 13, is made from a single die from a processed sheet metal or the like. For example, if the exterior shell 11 is metallic, such as aluminum, so are the one or more retaining devices 13. However, the retaining devices 13 alternatively may be made of a material other than that of the exterior shell 11, and subsequently connected to the exterior shell 11 using appropriate connecting means, such as adhesive, solder, clips, snapfit, or other means known in the art.

As described above, a sheet of resiliently compliable material 12 is positioned adjacent the exterior shell 11. This resiliently compliable material is silicone, rubber, foam, compressible pad, or any other material that may be generally compliant or exhibits, for example, substantially compressible properties. A resiliently compliable material 12 should be flexible enough to compress under manual force, while able to promote a seal between the plate 30 and a sealing member, such as the plastic sheet 35. Typical clamping forces of about 60 to 100 lbs over the surface of the whole plate 30 should compress the resiliently compliable material 12. The resiliently compliable material 12 may be separately manufactured and later applied or connected to the exterior shell 11 by an ultimate user. If separately manufactured, an adhesive may be coated on one side of the resiliently compliable material 12 and the adhesive may further be covered by a pealable protective sheet (not shown). This pealable protective sheet may then be removed to expose the adhesive and allow adhesion of one side of the resiliently compliable material 12 to the interior side of the exterior shell 11.

Alternatively, the resiliently compliable material 12 may be pre-manufactured affixed on the interior of the exterior shell 11 so that no further connection step is necessary. The resiliently compliable material 12 serves to support a seal in the wells 31 of a PCR plate 30 by pressing against the layer of clear plastic film 35 that has been layered above the wells 31 in the PCR plate 30, as described above with reference to FIG. 1. The resiliently compliable material 12 also optically separates the wells 31 from each other in the PCR tray 30 so that optical measurement of the well contents is not detrimentally distorted by signals from other wells.

The exterior shell 11 and the resiliently compliable material 12 preferably contain a plurality of holes 14 and 15, respectively. These holes 14, 15 are arranged in an array that correspond to the array of wells in PCR plates, such as wells 31 in PCR plates 30. Typical PCR plates may contain 96, 384, or 1536 total wells disposed in a rectangular array. However, any desirable number and arrangement of wells can be employed. As an example, the exemplary cover 10 shown in FIGS. 2–5 has 96 holes in a rectangular array, but other numbers or other positioning for the holes are also possible. The number and position of holes in the exterior shell/compliant pad should be related to the number and position of wells in a PCR plate to obtain correspondence and alignment of the holes to wells. Such correspondence of holes to wells may be one-to-one or multiple-to-one. Conversely, having multiple holes for each well may be possible but also may compromise optical measurements of the sample in the well when the well is covered by any material.

Care must be taken to ensure that the holes 14 in the exterior shell 11 align with holes 15 in the resiliently compliable material 12 during the connection of the two elements to promote optical detection of material in the wells 31 by automated real-time PCR reaction detectors, such as Models 7700 and 7900HT of Applied Biosystems of Foster City, Calif. Some optical detectors emit light from the top of the sample and through the holes 14 and 15, and subsequently measure reflected light from the sample. Other detectors may emit light to a sample in a well 31 from under the sample well 31 and subsequently measure transmitted light from the top of the sample through holes 14 and 15. Still other detectors, such as those disclosed in U.S. application Ser. No. 09/617,549, filed Jul. 14, 2000, and entitled "Scanning System and Method for Scanning a Plurality of Samples", which is hereby incorporated by reference in its entirety, promote dynamic scanning of multiple samples with an optical measurement device.

Exterior shell holes 14 and resiliently compliable material holes 15 are dimensioned to permit detecting equipment in a PCR system to optically analyze material within the wells 31 in the PCR plate 30 therethrough. Depending on the number of wells 31 for a given PCR plate 30, the size and shape of the holes 14 and 15 may fluctuate. For example, when a plate 30 has 96 or 384 wells, the holes 14 and 15 to its corresponding apparatus 10 or 20 may be round. The shape of the holes 14 and 15 should be more rectilinear as the number of wells 31 increases on the corresponding PCR plate to promote optical detection of the sample material in the wells of the plate by a detecting apparatus as described above. Thus, for a PCR plate 30 having 1536 or more wells, the holes 14 and 15 on a corresponding apparatus 10 or 20 may be square. Square holes allow for greater light passage than a round hole and are preferred with increasing numbers of holes 14 and 15 on a corresponding plate. However, this shape characteristic is not a requirement and, thus, any shape may be used for the holes 14 and 15 as long as enough light transmits through the holes to allow for optical detection. As an example, for a given 96 well plate, a hole 14 may have a diameter of about ⅛" and a pitch (center to center distance between holes) of about ⅜". As a further example, for a given 384 well plate, a hole 14 may have a diameter of about 0.2 mm and a pitch of about 0.45 mm. Other hole diameter sizes and pitch distances may be possible as long as the holes 14 and 15 function as described above.

Holes 14 and 15 both have centers on a single axis (not shown) that run vertically through the holes 14, 15 and is substantially perpendicular to the exterior shell 11. Holes 14, 15 also may have the same diameter. However, when a hole 15 has a larger diameter than a hole 14, optical reading, resolution, and analysis of material within the corresponding PCR plate well 31 through the holes 14, 15 are enhanced. This enhancement may result from the fact that when hole 15 has a larger diameter than hole 14, any excess adhesive between the exterior shell 11 and resiliently compliable material 12 is less likely to seep into and impede the optical path through the holes 14, 15, and thus dampen optimal optical analysis. Finally, as stated before, when the resiliently compliable material 12 is manufactured separately and then is attached to the exterior shell 11 by a suitable adhesive on one side of the resiliently compliable material 12, care should be given to align the holes 14 and 15 on the exterior shell 11 with the resiliently compliable material 12, respectively, to overlap and are concentric with common axes. The more accurate the placement of holes 14 and 15 on each other, then the more optimal the optical measurement of material within the plate wells can be.

Figure 5:
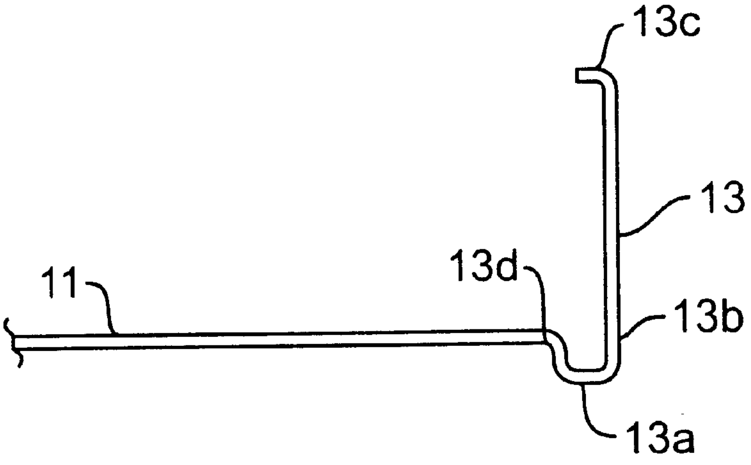
FIG. 5 is an enlarged fragmentary side view showing a retaining means of the apparatus of FIG. 4.

A retaining device 13 of the cover 10 is depicted in detail in FIG. 5. The retaining device 13 is connected to the exterior shell 11 (partially shown) at a C-shaped end 13*a*. The C-shaped end 13*a* allows the retaining device 13 to bend somewhat so that the retaining device 13 may fit around a PCR plate 30 or 40. However, the C-shaped end 13*a* must not be so flexible that it compromises the connection between the cover 10 and a PCR plate 30. Vertical support wall 13*b* typically may rest along the side of a PCR plate to allow an L-shaped end 13*c* to engage the bottom of the PCR plate. The retaining device 13 typically is constructed of resiliently flexible material, such as metal, plastic, or glass, as the exterior shell 11. Particular materials that are suitable for the retaining device 13 are those typically used for manufacturing a spring, including, for example, copper, aluminum, or polycarbonate. Because of its relative abundance, low cost and good heat transfer properties, aluminum may be the choice material for retaining device 13. If the retaining device 13 and the exterior shell 11 are made of different materials, then they may be connected at transition edge 13*d* by adhesive, snap fit, solder, or other means known in the art.

The resiliently compliable material 12 typically does not overlap onto the transition edge 13*d* so as to prevent any impedance on the flexibility of the retaining device 13. The retaining devices 13 of FIG. 1 typically wraps around and locks with the bottom side of the base 32 of plate 30 or the peripheral wall 42 of plate 40. The exterior shell 11 also may be sized to snugly fit into the tray-like area created by the top surface 43 and peripheral wall 42 such that the outer edges of the exterior shell 11 substantially correspond with an inner surface of the peripheral wall 42. Furthermore, retaining devices 13 may wrap around the peripheral wall 42 at the retaining device accommodating notches 44. Thus, alignment of the cover 10 with plate 40 is facilitated.

The retaining devices 13 are not limited to the shape and quantity depicted in FIGS. 2–5. They may be of any shape or quantity that permits suitable attachment to a typical PCR plate 30 or tray. The exemplary embodiment of FIGS. 2–5 is but just one example. Other configurations and quantity of retaining means 13 are also possible without departing from the scope of this invention. For example, FIGS. 6–9 illustrate another embodiment of this invention.

FIGS. 6–9 illustrate another exemplary embodiment the cover of the invention. The resiliently compliable material 12, depicted in FIGS. 2–5, is also suitable for the embodiment in FIGS. 6–9, and should have a number of holes 15 that correspond with the number of holes 24 in the exterior shell 21. The exterior shell 21 supports a layer of resiliently compliable material 12 and is substantially rigid and planar to maintain the structural integrity of a connected PCR plate 30 after thermal cycling. Retaining devices 23*a*, 23*b*, and 26 ensure a secure but releasable connection of the inventive apparatus 20 with a typical PCR plate 30. Finally, outermost edges 236 of each side of the retaining devices 23*a*, 23*b*, and 26 are sized such that they communicate with the ribs 36. Each retaining device 23*a*, 23*b*, and 26 by itself may fit snugly between corresponding ribs 36 on each side of the plate 30 to promote increased alignment between the apparatus 20 and the plate 30.

As with the embodiment depicted in FIGS. 2–5, the materials used to construct the embodiment depicted in FIGS. 6–9 also may be metal, plastic, ceramic, glass, or others that are substantially rigid but flexible enough to attach and detach from a PCR plate. Furthermore, the exterior shell 21 and the retaining devices 23*a*, 23*b*, and 26 all may be the same or different materials, or some combination. For example, the exterior shell may be glass, the retaining devices 23*a*, 23*b* may be plastic, and the retaining device 26 may be metal. The cover 20 depicted in FIG. 6 preferably may be a unitary structure entirely made of a metal, such as aluminum, such that manufacturing costs are minimized. A unitary structure also ensures uniformity in quality product and prevents additional steps in connecting various parts together, ensuring time and cost savings. The cover 20 may be made by a die method, known in the art.

Figure 6:
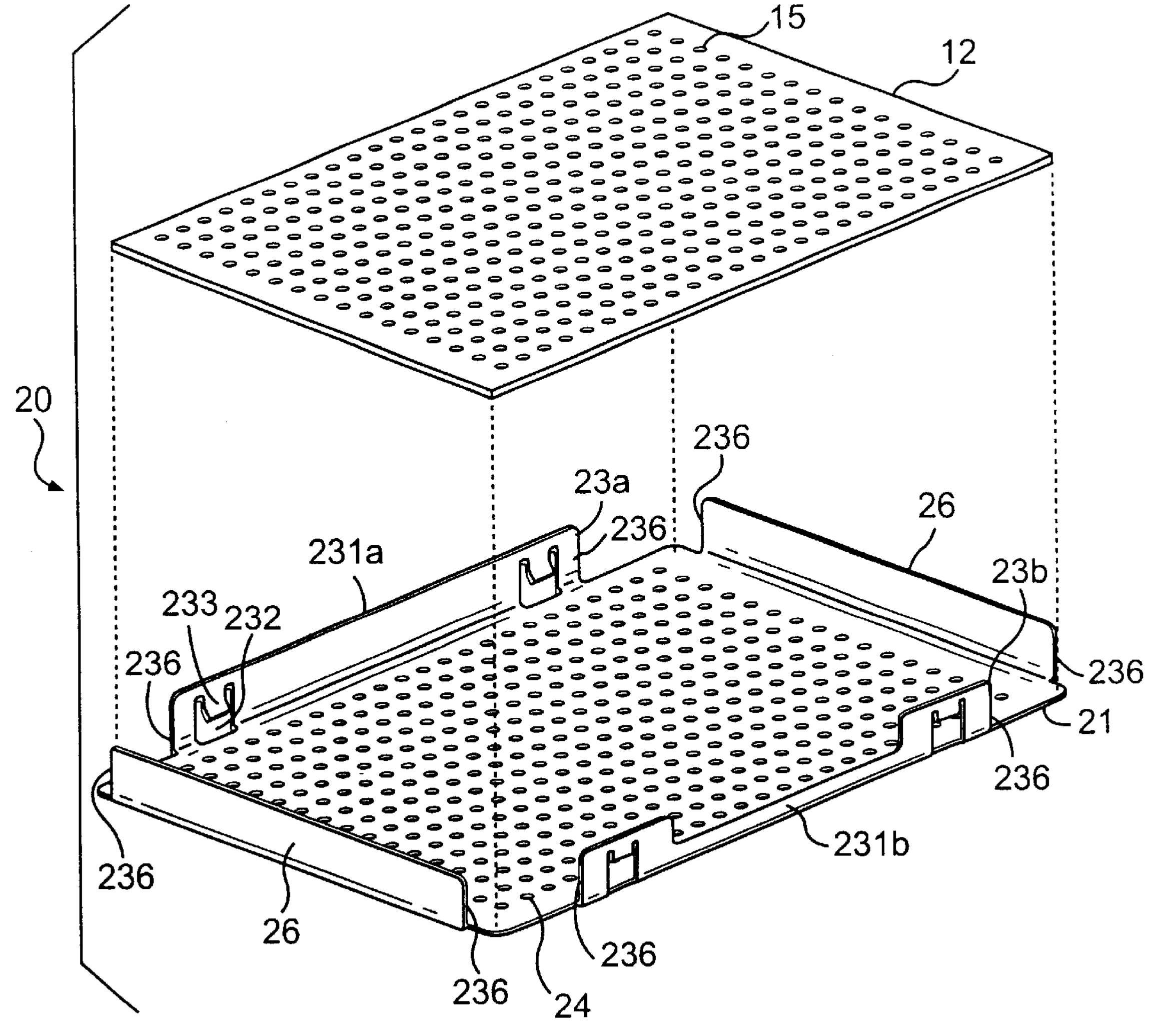
FIG. 6 is a perspective view of an alternative 384-well embodiment of the present i; invention.

The exterior shell 21 may contain an array of holes 24 arranged in predetermined numbers corresponding to wells in a typical PCR plate. The embodiment shown in FIG. 6 presents 384 wells by example but any other number of holes also may be possible.

The retaining devices 23*a* and 23*b* are substantially similar to each other but with distinctions as described below. They both include a central support wall 231 having one or more apertures 232 therein. The apertures 232 act as a frame for a retention clip 233 contained therein. The support walls 231 may be a full wall 231*a*, as in retaining device 23*a*, or a half wall 231*b*, as in retaining device 23*b*. The half wall 231*b* provides a window to overly identifying indicia, such as a bar code (not shown) centered on a corresponding side wall, e.g., 34*b* of the PCR plate 40.

The other pair of retaining devices 26 may be alignment walls that also provide structural support to a PCR plate 30. The alignment walls 26 may be made of the same or different material from the exterior shell 21. Furthermore, the alignment walls 26, as well as the support walls 231*a*, 231*b*, in addition to providing structural integrity to the apparatus 20 when attached to a PCR plate, also serve to block out exterior sources of light that may affect and distort optical readings from material within the wells in a PCR plate.

Figure 9:
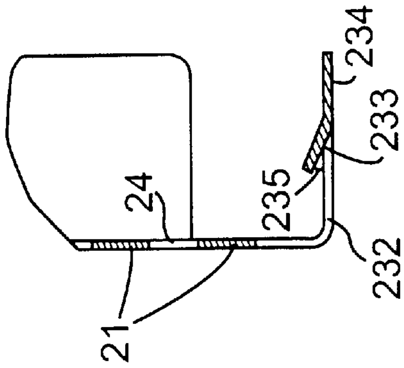
FIG. 9 is an enlarged fragmentary side view of a retaining means in the embodiment of FIG. 6.
Figure 7:
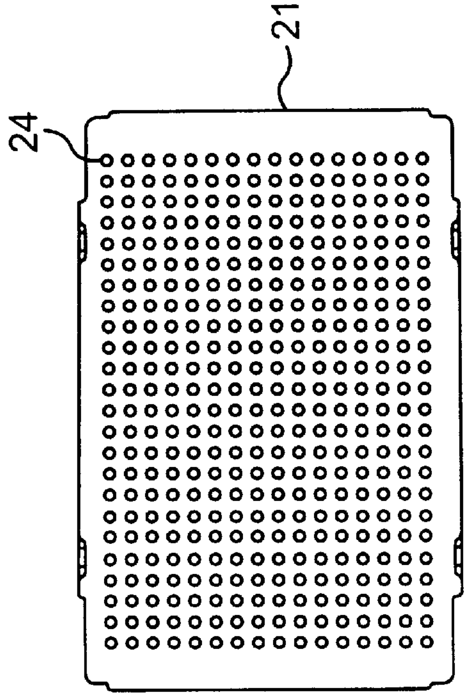
FIG. 7 is a bottom plan view of the apparatus of FIG. 6.
Figure 8:
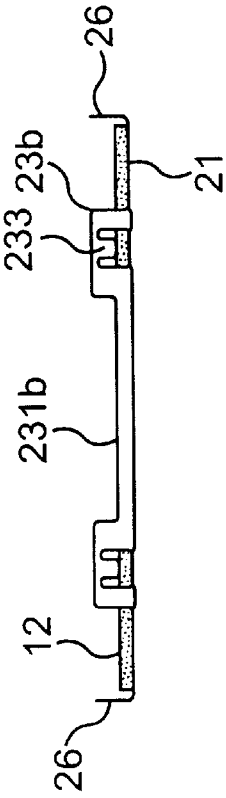
FIG. 8 is a side view of the apparatus of FIG. 6.

Each of the retaining devices 23*a*, 23*b* may contain one or more apertures 232. Each aperture 232 further may frame at least one retention clip 233 within. FIG. 9 depicts a more detailed illustration of a retention clip 233, which is slightly angled to better grip a PCR plate. A hanging wall 234 connects the retention clip 233 to a side wall 34*b* of the PCR plate 30 and enables the retention clip 233 to engage the side wall 34*b*. The retention clip 233 may be offset at an angle 235 from the plane of the hanging wall 234. The angled configuration of the retention clip 233 permits the clip to be substantially directed into and engage the side wall 34*b* of a PCR plate 30, thereby securing the inventive apparatus 20 to a PCR plate 30 by friction fit, or by interlocking engagement in the apertures 33 of the plate 30 shown in FIG. 1*a*. Such an angle 235 may be about 15 to 45 degrees. At about 15 degrees, there may be less spring force, but greater strength. At about 45 degrees, there may be greater spring force but a compromise in strength. At the latter angle, there also may be greater possibility of the clip 233 jamming and breaking.

A desirable range for angle 235 may be about 20 to 30 degrees for aluminum, but the range is mostly dependent on the nature of the material used for the clip 233.

The design of the retention clips 233 allows the cover 20 to be secured to the PCR plate 30 by simply pressing the cover 20 onto the plate 30. In this respect, the ribs 36 provide precise alignment of the holes 14, 15 in the cover 20 with the respective wells 31 in the PCR plate. In particular, the ribs 36 on the sides of the plate 30 engage the walls 231*a* and 231*b* of the cover 20 adjacent the apertures 232 therein to position the cover 20 laterally with respect to the PCR plate 30. In like manner, the ribs 36 on the ends of the PCR plate 30 engage the walls 26 of the cover 20 for relative longitudinal alignment. The resulting positional alignment of the cover 20 and the PCR plate 30 is particularly important where the number of wells 31 in the plate 30 is 384 or more.

Although an exemplary embodiment of a retention clip 233 has been presented in the figures, other configurations are also possible without departing from the scope of this invention. For example, C-shaped clips, L-shaped clips, hooks, or other similar devices, typically with projections that have an end pointing into and frictionally engaging a side wall of a PCR plate 30 also may be used to secure the inventive apparatus 20 to a PCR plate 30 or 40.

A further embodiment of the invention is shown in FIGS. 10–14, in which parts previously described are designated by reference numerals having the same tens and digits numbers but in a "300" series. Thus, the cover 310 is shown to include the same exterior shell 311 and holes 314 of the previous embodiments. In this instance, however, the retaining devices 313 are elongated and spaced on opposite sides, respectively, of the rectangular shell 311 but have the same L-shaped end profile as the retaining devices in the embodiment of FIGS. 2–5. Also retaining devices 326, which position the shell 311 lengthwise of a PCR plate or tray, depend from the ends of the shell 311, completely across the width of the shell 311. Thus, the shell 311 of the apparatus 310 has an enhanced measure of marginal support provided both by the continuity of the retaining devices 326 across the ends thereof, and by the lengthened, though spaced, configuration of the retaining devices 313 along the sides of the shell 311. In all other respects, the previous descriptions of the embodiments of FIGS. 2–5 and of FIGS. 6–9 apply to the embodiment of FIGS. 10–14.

Another exemplary embodiment of this invention is a PCR processing assembly that contains a PCR plate, for example, as generally depicted in FIG. 1, and a corresponding cover, for example, any one of the covers 10, 20 or 310. The assembly would include both the plate 30 or 40 and a corresponding locking cover 10 or 20. Thus, this could reduce the necessity to match a particular cover to existing PCR plates. A purchaser could be able to obtain the assembly as a whole and could save time in matching parts. The purchaser typically could use a conventional heat shrink sheet or adhesive sheet to layer over the wells of the PCR plate and then support the layer with a cover, for example apparatus 10 or 20 as depicted above.

Although the invention has been described with the exemplary embodiments shown, other embodiments are also within the teaching of this invention. For example, the cover apparatus 10 or 20 may be made to swing on a hinge on one side of the apparatus and connected to a corresponding side of the plate, and various retaining means to lock the cover apparatus to the plate. This embodiment would eliminate the need for two components to the PCR assembly. Furthermore, the entire exterior shell 11 or 21 may be a translucent material, such as glass, thus eliminating the need for holes 14, 24, respectively. Finally, either of the apparatus 10 or 20 may be a shape other than planar and flat, such as curvilinear, angled, or curved, to accommodate a similarly-shaped sample holding apparatus.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A cover for retaining a sealing sheet on a surface of a PCR plate, wherein the PCR plate has sample wells depending from and opening through the surface and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells;

a plurality of holes in the substantially rigid sheet and in the resiliently compliable sheet, each hole being of a size and shape capable of allowing optical access therethrough; and at least one retaining device attached to the substantially rigid sheet and engagable with the PCR plate to retain the substantially rigid sheet and the resiliently compliable sheet in a condition to press the sealing sheet against the surface of the PCR plate.

2. The cover of claim 1, wherein each said hole is arranged so as to correspond to and align with a respective well of the PCR plate.

3. A cover for retaining a sealing sheet on a surface of a PCR plate, wherein the PCR plate has sample wells depending from and opening through the surface, and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the resiliently compliable sheet is attached to the substantially rigid sheet with an adhesive.

4. A cover for retaining a sealing sheet on a surface of a PCR plate, wherein the PCR plate has sample wells depending from and opening through the surface, and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the resiliently compliable sheet is pre-manufactured with one side having an adhesive thereon, and covered by a pealable sheet.

5. A cover for retaining a sealing sheet on a surface of a PCR plate wherein the PCR plate has sample wells depending from and opening through the surface, and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the at least one retaining device extends from an edge of the substantially rigid sheet, and wherein the at least one retaining device further is substantially perpendicular to the substantially rigid sheet.

6. The cover of claim 5, wherein the at least one retaining device further includes an L-shaped projection to releasably engage the base of the PCR plate.

7. The cover of claim 6, wherein the cover and the PCR plate are rectangular to provide opposite sides and opposite ends on the respective substantially rigid sheet and PCR plate and including the at least one retaining device on the opposite sides of the substantially rigid sheet.

8. The cover of claim 7, wherein the at least one retaining device further comprises a retaining device on each of the opposite ends of the substantially rigid sheet.

9. The cover of claim 6, wherein the at least one retaining device is provided in a wall depending from each side of the substantially rigid sheet.

10. The cover of claim 9 including a pair of spaced retaining devices in the wall depending from each side of the substantially rigid sheet, the wall extending along substantially the full length of each side of the substantially rigid sheet and being substantially perpendicular thereto.

11. The cover of claim 10, wherein each of said retaining devices further comprises a clip projecting at an angle from the depending wall such that the clip is adapted to engage a peripheral wall of the PCR plate.

12. The cover of claim 11, wherein the angle is about 20 to 45 degrees.

13. The cover of claim 12, wherein the angle is about 20 to 30 degrees.

14. The cover of claim 13 including a depending wall at each end of the substantially rigid sheet to position the cover lengthwise on the PCR plate.

15. The cover of claim 14, wherein the depending wall at each end of the substantially rigid sheet is substantially perpendicular thereto.

16. A cover for retaining a sealing sheet on a surface of a PCR plate, wherein the PCR plate has sample wells depending from and opening through the surface, and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the substantially rigid sheet substantially fits into a space defined by the surface of the PCR plate and the peripheral wall of the PCR plate.

17. A cover for retaining a sealing sheet on a surface of a PCR plate, wherein the PCR plate has sample wells depending from and opening through the surface, and a peripheral wall surrounding the sample wells and connected to a base, the cover comprising:

a substantially rigid sheet capable of maintaining the surface of the PCR plate in a pre-thermal-cycling shape during a PCR thermal cycling process;

a resiliently compliable sheet cooperable with one side of the substantially rigid sheet to press the sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the at least one retaining device aligns with ribs located on the peripheral wall of the PCR plate.

18. Apparatus for processing samples in PCR, comprising:

a PCR plate having sample wells depending from and opening through a surface in the plate, and a peripheral wall surrounding the sample wells and connected to a base;

a cover for the PCR plate, the cover comprising:

a substantially rigid sheet capable of maintaining the surface of the PCR plate in a pre-thermal-cycling shape during a PCR thermal cycling process;

a resiliently compliable sheet cooperating with one side of the substantially rigid sheet and capable of pressing a sealing sheet against the surface of the PCR plate to maintain a seal in the wells; and at least one retaining device attached to the substantially rigid sheet and engagable with the PCR plate to retain the substantially rigid sheet and the resiliently compliable sheet in a condition to press the sealing sheet against the surface of the PCR plate, wherein the substantially rigid sheet and the resiliently compliable sheet have holes alignable with the respective sample wells in the PCR plate, each of the holes being of a size and shape allowing optical access through the cover to the sample wells.

19. The apparatus of claim 18 including means for aligning the holes in the cover with the sample wells in the PCR plate.

20. The apparatus of claim 19, wherein the cover has peripheral walls and the means for aligning the holes in the cover with the sample wells in the PCR plate comprises ribs on the peripheral walls of the PCR plate engageable with the peripheral walls of the cover.

21. The cover of claim 1, wherein the resiliently compliable sheet is attached to the substantially rigid sheet with an adhesive.

22. The cover of claim 1, wherein the resiliently compliable sheet is pre-manufactured with one side having an adhesive thereon, and covered by a pealable sheet.

23. The cover of claim 1, wherein the at least one retaining device extends from an edge of the substantially rigid sheet.

24. The cover of claim 23, wherein the at least one retaining device further is substantially perpendicular to the substantially rigid sheet.

25. The cover of claim 24, wherein the at least one retaining device further includes an L-shaped projection to releasably engage the base of the PCR plate.

26. The cover of claim 25, wherein the cover and the PCR plate are rectangular to provide. opposite sides and opposite ends on the respective substantially rigid sheet and PCR plate and including the at least one retaining device on the opposite sides of the substantially rigid sheet.

27. The cover of claim 26, wherein the at least one retaining device further comprises a retaining device on each of the opposite ends of the substantially rigid sheet.

28. The cover of claim 25, wherein the at least one retaining device is provided in a wall depending from each side of the substantially rigid sheet.

29. The cover of claim 28, including a pair of spaced retaining devices in the wall depending from each side of the substantially rigid sheet, the wall extending along substantially the full length of each side of the substantially rigid sheet and being substantially perpendicular thereto.

30. The cover of claim 29, wherein each of said retaining devices further comprises a clip projecting at an angle from the depending wall such that the clip is adapted to engage a peripheral wall of the PCR plate.

31. The cover of claim 30, wherein the angle is about 15 to 45 degrees.

32. The cover of claim 31, wherein the angle is about 20 to 30 degrees.

33. The cover of claim 32, including a depending wall at each end of the substantially rigid sheet to position the cover lengthwise on the PCR plate.

34. The cover of claim 33, wherein the depending wall at each end of the substantially rigid sheet is substantially perpendicular thereto.

35. The cover of claim 1, wherein the substantially rigid sheet substantially fits into a space defined by the surface of the PCR plate and the peripheral wall of the PCR plate.

36. The cover of claim 1, wherein the at least one retaining device overlies a notch in the peripheral wall of the PCR plate.

37. The cover of claim 1, wherein the at least one retaining device aligns with ribs located on the peripheral wall of the PCR plate.

* * * * *

UNITED STATES PATENT AND TRADEMARK OFFICE

CERTIFICATE OF CORRECTION

PATENT NO. : 6,426,215 B1
DATED : July 30, 2002
INVENTOR(S) : Donald R. Sandell

It is certified that error appears in the above-identified patent and that said Letters Patent is hereby corrected as shown below:

<u>Column 10,</u>
Line 15, after "surface" insert -- , --.

<u>Column 11,</u>
Line 12, after "plate" (first occurrence) insert -- , --.
Line 56, "about 20" should read -- about 15 --.

<u>Column 13,</u>
Line 19, after "provide" delete "."

<u>Column 14,</u>
Line 13, after "claim 32" delete ",".

Signed and Sealed this

Twenty-ninth Day of October, 2002

*Attest:*

JAMES E. ROGAN

*Attesting Officer*

*Director of the United States Patent and Trademark Office*